United States Patent [19]

Kikuchi

[11] Patent Number: 4,610,828

[45] Date of Patent: Sep. 9, 1986

[54] PROCESS FOR PREPARING L-CARNITINE AND SALTS THEREOF

[75] Inventor: Haruhiko Kikuchi, Kamifukuoka, Japan

[73] Assignees: Nisshin Flour Milling Co., Ltd.; Nisshin Chemicals Co., Ltd., both of Japan

[21] Appl. No.: 783,872

[22] Filed: Oct. 3, 1985

[30] Foreign Application Priority Data

Oct. 9, 1984 [JP] Japan ................................ 59-210442

[51] Int. Cl.$^4$ .............................................. C07B 57/00
[52] U.S. Cl. .................................. 260/501.13; 562/401
[58] Field of Search ..................................... 260/501.13

[56] References Cited

U.S. PATENT DOCUMENTS 3,832,388  8/1974  Lorenz ................................ 562/401

FOREIGN PATENT DOCUMENTS 1513328  1/1968  France .

*Primary Examiner*—Natalie Trousof
*Assistant Examiner*—Vera C. Clarke
*Attorney, Agent, or Firm*—Abelman Frayne Rezac & Schwab

[57] ABSTRACT

L-carnitine and salts thereof are resolved from DL-carnitine by the use as a resolving agent of dibenzoyl-L(+)tartaric acid. L-carnitine is known as vitamin $B_T$ and is useful as a medicine.

8 Claims, No Drawings

PROCESS FOR PREPARING L-CARNITINE AND SALTS THEREOF

FIELD OF THE INVENTION

This invention relates to processes for preparing L-carnitine and salts thereof from DL-carnitine by the use as a resolving agent of dibenzoyl-L(+)tartaric acid.

BACKGROUND OF THE INVENTION

L-carnitine is known as vitamin $B_T$ and chemically termed L-$\gamma$-amino-$\beta$-hydroxybutyric acid trimethylbetain.

L-carnitine known as vitamin $B_T$ exists in tissues of many living organisms, including microorganism to human being, and is an indispensable factor for the growth of dark mealworm (*Tanebrio obscurus Fabricius*). For this reason, various studies have recently been made with regard to its physiological activities and clinical application (See S. L. De Felice, Orphan Drugs, F. E. Karch, Ed. C. Marcel Dekker, New York, 1982, pp. 33-56). Under such circumstances, it has already been known that D-carnitine competitively inhibits the physiological activities of L-carnitine, though carnitine has been synthesized as DL-carnitine chloride on an industrial scale. Therefore, an effective method of resolving DL-carnitine has been desired.

In this connection, a method of optical resolution of DL-carnitine has been disclosed in East German Patent No. 93347 specification, wherein L(+)tartaric acid, dibenzoyl-D(−)tartaric acid, D(+)camphoric acid and D(−)camphoric acid are recited as resolving agents. This prior art method, however, involves a problem in its application to industrial production of L-carnitine, because the resolving agents used therein are relatively expensive and L-carnitine of high purity is difficult to obtain.

SUMMARY OF THE INVENTION

A principal object of the present invention is to provide processes for preparing on an industrial scale L-carnitine and salts thereof in high purity from DL-carnitine.

Other objects and advantages of the invention will become apparent from the following description of one practical embodiment of the invention.

Now, the present inventor has studied extensively the optical resolution of DL-carnitine and has found surprisingly that L-carnitine of high purity can be prepared in a simple manner by using as a resolving agent dibenzoyl-L(+)tartaric acid which is relatively inexpensive because of its synthesis from naturally occurring L(+)tartaric acid.

In accordance with the present invention, L-carnitine can be prepared by reacting DL-carnitine with dibenzoyl-L(+)tartaric acid as a resolving agent to form dibenzoyl-L(+)tartarates of D-carnitine and L-carnitine, fractionally crystallizing from said tartarates dibenzoyl-L(+)tartarate of L-carnitine, and subsequently decomposing the tartarate to give L-carnitine.

DESCRIPTION OF PREFERRED EMBODIMENTS

According to a preferred embodiment of the present invention, in the first step, to DL-carnitine is added dibenzoyl-L(+)tartaric acid and a lower alcohol, the mixture is dissolved under heat to form dibenzoyl-L(+)tartarates of D-carnitine and L-carnitine, and subsequently the tartarates are cooled to fractionally crystallize dibenzoyl-L(+)tartarate of L-carnitine.

Dibenzoyl-L(+)tartaric acid used as a resolving agent is inexpensive, since it can be synthesized from naturally occurring L(+)tartaric acid. In contrast, dibenzoyl-D(−)tartaric acid disclosed in East German Patent No. 93347 specification is expensive resolving agent, since D(−)tartaric acid per se does not exist in nature and its dibenzoyl compound can be only synthetically prepared. Further, dibenzoyl-L(+)tartaric acid can achieve the effect of giving higher purity in the crystallizing L-carnitine dibenzoyl-L(+)tartarate, as compared with dibenzoyl-D(−)tartaric acid. The amount of dibenzoyl-L(+)tartaric acid used as the resolving agent is 0.7–1.5 times, preferably equal to that of DL-carnitine.

The lower alcohol used for fractional crystallization of L-carnitine dibenzoyl-L(+)tartarate from dibenzoyl-L(+)tartarates of D-carnitine and L-carnitine includes methanol, ethanol and the mixture thereof, and preferably methanol. Fractional crystallization is conducted at a temperature of from 5° C. to −20° C. Further, fractional crystallization conducted at a temperature of below −10° C. can achieve more improved crystallization of L-carnitine dibenzoyl-L(+)tartarate.

In the second step of the present invention, dibenzoyl-L(+)tartarate of L-carnitine obtained by fractional crystallization is recrystallized with use of a polar solvent. The polar solvent includes methanol, ethanol, isopropanol or the mixtures thereof, and methanol and ethanol are preferred.

In the third step of the present invention, dibenzoyl-L(+)tartarate of L-carnitine is decomposed in the usual way, e.g., with water, preferably acidic water to obtain the desired L-carnitine. If necessary, L-carnitine may be converted in the usual way to its salt.

The following examples typify the manner by which the present invention can be practiced and represent in one aspect the best mode for carrying out the invention. As such, they should be construed merely as illustrative and not as limitative upon the overall scope thereof.

EXAMPLE 1

A solution of 35.0 g (0.177 mole) of DL-carnitine hydrochloride in 300 ml of water is passed through OH type strongly basic resin (Dowex-1X8) and the solution is concentrated to give 28.0 g (0.173 mole) of DL-carnitine. To DL-carnitine are added 61.9 g (0.173 mole) of dibenzoyl-L(+)tartaric acid and 90 ml of methanol. The mixture is dissolved under heat to form dibenzoyl-L(+)tartarates of D-carnitine and L-carnitine. The tartarates are cooled from 60° C. to 5° C. over a period of 24 hours to fractionally crystallize L-carnitine dibenzoyl-L(+)tartarate. The tartarate is filtered and washed to give L-carnitine dibenzoyl-L(+)tartarate (yield 39.0 g, purity 92.7%). The tartarate obtained is dissolved under heat in 190 ml of ethanol, and cooled from 60° C. to 25° C. over a period of 24 hours. This recrystallization gives 21.5 g of crystals of L-carnitine dibenzoyl-L(+)tartarate. $[\alpha]_D^{25} = -96.2°$ (c=1, MeOH), m.p. 154° C. (dec.), purity 99.7%.

To the crystals are added 30 ml of water and 100 ml of ethyl acetate, and the mixture is vigorously stirred to decompose L-carnitine dibenzoyl-L(+)tartarate. The organic layer containing the recovered resolving agent is removed therefrom, and the aqueous layer containing L-carnitine, after treatment with the strongly basic resin, is charged with 3.5 ml of concentrated hydrochloric acid and then concentrated under reduced pressure. Recrystallization of the residue from ethanol gives 8.6 g (0.044 mole) of L-carnitine hydrochloride as white crystal. $[\alpha]_D^{25} = -23.7°$ (c=2, H$_2$O), m.p. 142° C.

EXAMPLE 2

In 700 ml of methanol are dissolved under heat 35.0 g (0.177 mole) of DL-carnitine hydrochloride, and the solution is passed through OH type strongly basic resin (DOWEX-1X8). The methanol solution is concentrated to obtain 28.3 g (0.175 mole) of DL-carnitine. To DL-carnitine are added 62.6 g (0.175 mole) of dibenzoyl-L(+)tartaric acid and 93 ml of methanol, and the mixture is dissolved under heat to form dibenzoyl-L(+)tartarates of D-carnitine and L-carnitine. The tartarates are cooled at a temperature of below −10° C. with stirring to fractionally crystallize L-carnitine dibenzoyl-L(+)tartarate. The tartarare is filtered and washed to give L-carnitine dibenzoyl-L(+)tartarate (yield 30.5 g, purity 93.0%). Recrystallization of the tartarate from 100 ml of methanol gives 23.9 g of L-carnitine dibenzoyl-L(+)tartarate as white crystal. $[\alpha]_D^{25} = -96.0°$ (c=1, MeOH), m.p. 154° C. (dec.), purity 99.5%.

The crystal is suspended in 60 ml of acetone and, after passing about 1.7 g of hydrogen chloride gas therethrough, the suspension is stirred for 1 hour at room temperature, and the reaction liquid is filtered to obtain 8.8 g (0.045 mole) of L-carnitine hydrochloride as white crystal. $[\alpha]_D^{25} = -23.30°$, (c=2, H$_2$O), m.p. 142° C.

What is claimed is:

1. A process for preparing L-carnitine and the salts thereof which comprises reacting DL-carnitine with dibenzoyl-L(+)tartaric acid as a resolving agent to form dibenzoyl-L(+)tartarates of D-carnitine and L-carnitine, fractionally crystallizing from said tartarates dibenzoyl-L(+)tartarate of L-carnitine, and subsequently decomposing the tartarate to give L-carnitine, and if necessary converting it to the salts thereof.

2. The process of claim 1 wherein fractional crystallization is conducted in a lower alcohol.

3. The process of claim 2 wherein the lower alcohol is methanol.

4. The process of claim 1 wherein fractional crystallization is conducted at a temperature of from 5° C. to −20° C.

5. The process of claim 4 wherein fractional crystallization is conducted at a temperature of below −10° C.

6. The process of claim 1 wherein dibenzoyl-L(+)tartarate of L-carnitine is also recrystallized with the use of a polar solvent.

7. The process of claim 6 wherein the polar solvent is ethanol.

8. The process of claim 6 wherein the polar solvent is methanol.

* * * * *